(12) United States Patent
Välimaa et al.

(10) Patent No.: US 6,709,452 B1
(45) Date of Patent: Mar. 23, 2004

(54) BIODEGRADABLE SURGICAL IMPLANTS

(75) Inventors: Tero Välimaa, Tampere (FI); James Hogan, Blue Bell, PA (US)

(73) Assignee: Linvatec Biomaterial Oy, Tampere (FI)

( * ) Notice: Subject to any disclaimer, the term of this patent is extended or adjusted under 35 U.S.C. 154(b) by 0 days.

(21) Appl. No.: 09/641,706

(22) Filed: Aug. 21, 2000

(51) Int. Cl.$^7$ .................................................. A61F 2/06
(52) U.S. Cl. ....................................................... 623/1.15
(58) Field of Search ................................ 623/1.1, 1.11, 623/1.12, 1.13, 1.14, 1.15, 1.16, 1.17, 1.18, 1.19, 1.2, 1.38, 1.39, 1.42, 1.43, 1.44, 1.45; 606/191, 194, 198, 192

(56) References Cited

U.S. PATENT DOCUMENTS

| | | | |
|---|---|---|---|
| 5,443,458 A | * 8/1995 | Eury ........................ | 604/891.1 |
| 5,464,450 A | * 11/1995 | Buscemi et al. ................ | 623/6 |
| 5,527,337 A | * 6/1996 | Stack et al. .................. | 606/198 |
| 5,629,077 A | 5/1997 | Turnlund et al. .............. | 442/38 |
| 5,957,975 A | 9/1999 | Lafont et al. ................... | 623/1 |
| 6,117,168 A | * 9/2000 | Yang et al. ................. | 623/1.44 |
| 6,228,111 B1 | * 5/2001 | Tormala et al. ............ | 623/1.38 |
| 6,338,739 B1 | * 1/2002 | Datta et al. ................. | 623/1.15 |
| 6,368,346 B1 | * 4/2002 | Jadhav ...................... | 623/1.22 |

* cited by examiner

*Primary Examiner*—Vy Q. Bui
(74) *Attorney, Agent, or Firm*—Kenyon & Kenyon

(57) ABSTRACT

A biodegradable implant for installation in living tissue having a first section made from a first bioabsorbable material and a second section made from a second bioabsorbable material, wherein the first and second sections are connected, the first section having a first rate of degradation in living tissue and a first rate of expansion in living tissue and the second section having a second rate of degradation in living tissue and a second rate of expansion in living tissue.

23 Claims, 4 Drawing Sheets

BIODEGRADABLE SURGICAL IMPLANTS

FIELD OF THE INVENTION

The present invention relates to biodegradable surgical implants.

BACKGROUND OF THE INVENTION

This application relates to U.S. application Ser. No. 09/465,789, filed on Dec. 17, 1999, relating to a device for inserting stents. The disclosure of that patent application is hereby incorporated by reference in its entirety.

In surgery, it is known to employ biodegradable, elongated (typically tubular) surgical implants for supporting, connecting or separating elongated organs, tissues or parts thereof, such as canals, ducts, tubes, intestines, blood vessels, nerves etc. The biodegradable material degrades in vivo and the dissolution products leave the system, e.g., through metabolic ducts, kidneys, lungs, intestines and/or skin by secretion.

Tubular, biodegradable surgical implants involve several drawbacks and limitations, migration being one of them. An injury being treated with a bioabsorbable implant will only heal properly if the implant remains in its intended location within the body, i.e., if the implant does not migrate after implantation. The implants manufactured with previously-known techniques and biodegradable materials do not necessarily prevent migration because they often do not attach themselves tightly enough to the walls of the body cavity, e.g., a blood vessel, being treated.

U.S. Pat. No. 5,792,400 to Talja et al. is related to a method of producing a surgical implant or part thereof made of biodegradable material for supporting, joining and separating tissue and keeping open a tissue cavity. The surgical implant has a helical configuration. However, those biodegradable materials having suitable degradation rates to be used for healing the injury normally have a rather long period of self-expanding after the insertion, which increases the risk that the implant will migrate after insertion.

WO 97/11724 to Törmälä et al. also discloses a biodegradable implant. The macroscopic structure of the implant comprises two or several zones, which are created in a manner that they have different degradation times. This technique does not, however, define any preparatory measures for achieving functional modification of the surgical implant, for instance, the self-expansion property of the implant, in order to prevent migration of the implant.

SUMMARY OF THE INVENTION

It has been surprisingly discovered in this invention that the migration of biodegradable surgical implants used for supporting, connecting or separating organs, tissues or parts thereof can be substantially eliminated. This invention relates to a biodegradable implant or the like manufactured of polymer-based material and intended to be installed in vivo. The biodegradable implant comprises at least two sections manufactured of different polymer-based materials and joined together to form at least a part of the implant, wherein the first section has first period of degradation and self-expansion in vivo, and the second section has second period of degradation and self-expansion in vivo.

By using the implant of the present invention and selecting the periods of degradation and self-expansion appropriately, it is possible to ensure a rapid and firm fixing of the implant after its installation. The second portion of the implant will rapidly expand, thereby affixing the implant securely in its intended location, e.g., a blood vessel or other duct. The first section of the implant, which degrades more slowly than the second section of the implant, will expand more slowly than the second section of the implant. While the first section of the implant is expanding, the second section of the implant, which has already expanded, is helping to ensure that the implant does not migrate. Once the first section of the implant has expanded and is affixed securely in its intended location, it will provide the longer-lasting structural support that is needed. Once the first section of the implant has expanded and has affixed itself to the intended location, the second section of the implant may biodegrade, leaving the first section of the implant in place.

BRIEF DESCRIPTION OF THE DRAWINGS

The invention is described in more detail in the following specification with reference made to the accompanying drawings. In the drawings.

DETAILED DESCRIPTION OF PREFERRED EMBODIMENTS

Figure 1:
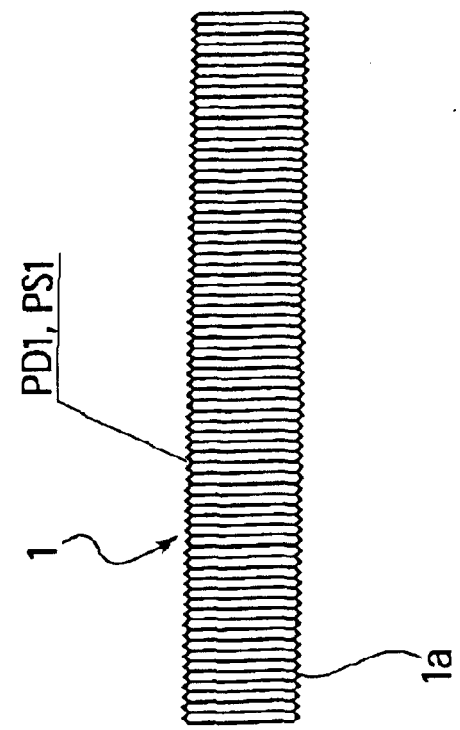
FIG. 1 shows in a side planar view of an embodiment of an implant according to the invention prior to the connection of the first and second sections (also referred to in example 3)
Figure 1:
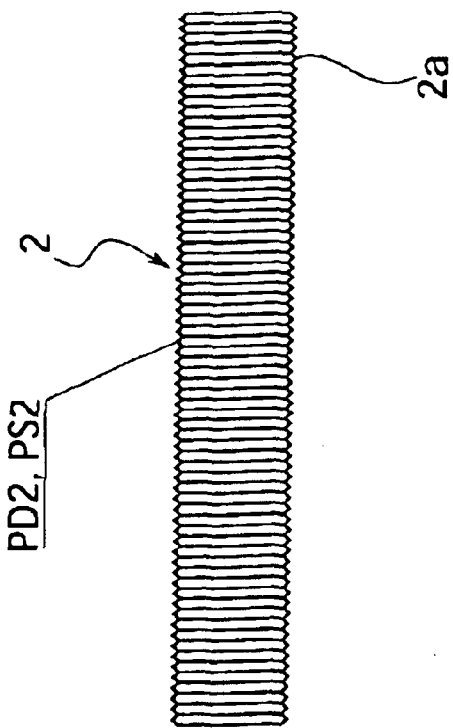

FIG. 1 shows a biodegradable implant comprising two coiled helical sections, forming a first proximal section and a second distal section, 1 and 2, respectively, of the implant (referred to herein as "first section" and "second section"). The coiled sections are manufactured of different polymer-based materials. The implant is intended to be installed in vivo, e.g. inside a blood vessel or a vein to treat or prevent an obstruction.

Section 1 has a period of degradation PD1 and a period of self-expansion PS1. Similarly, section 2 has a period of degradation PD2 and a period of self-expansion PS2. By manufacturing the first and second sections 1 and 2 from compatible polymer-based materials, it is possible to create an implant in which the period of degradation PD1 of section 1 is longer than the period of degradation PD2 of section 2. Further, the period of self-expansion PS1 of section 1 is longer than the period of self-expansion PS2 of section 2. Thus, section 2 will expand and degrade faster than section 1.

Figure 3:
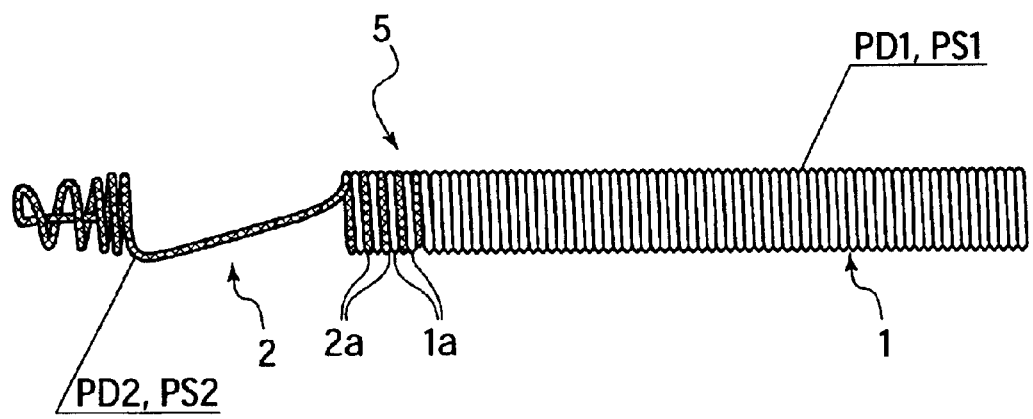
FIG. 3 shows in a side planar view of the second embodiment of the implant according to the invention after the connection of the first and second sections.

The two sections 1 and 2 of FIG. 1 are joined together to form at least a part of the implant. To achieve this, end portions 1a and 2a of sections 1 and 2 are locked together, thereby connecting the two sections 1 and 2. This may be done, e.g., by intertwining the coils of end portions 1a and 2a. This may be accomplished simply by pushing the end sections 1a and 2a against each other and twisting them together around their mutual longitudinal center line, such that the end portions 1a and 2a protrude into each other and overlap in the spaces between the successive adjacent rounds of the helical coil formation. Such an overlap is shown in FIG. 3 with reference numeral 5. Section 2, however, should not expand so much, so fast, that it separates from section 1 prior to the expansion of section 1.

Figure 4:
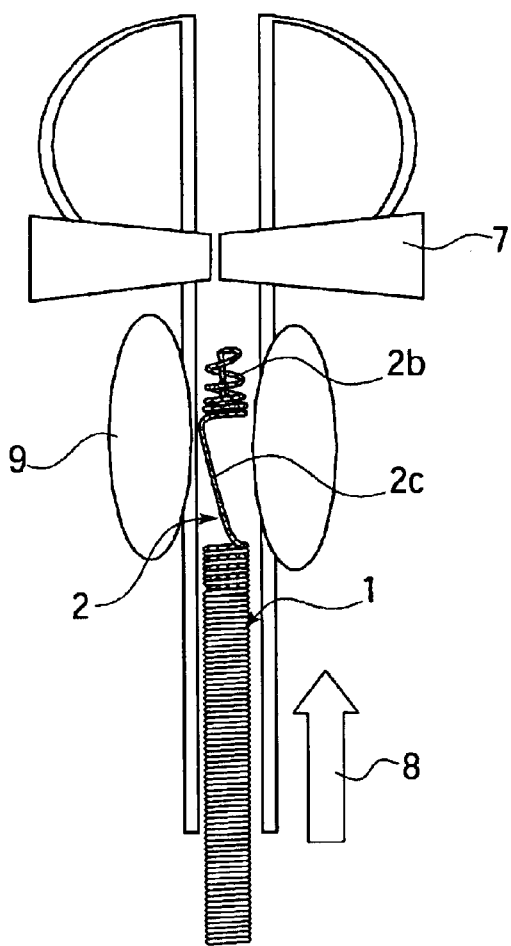
FIG. 4 shows a side schematically planar view of the implant according to FIG. 3 during installation into the urethra, FIG. 5 further shows a side schematically planar view of the implant according to FIG. 3 after installation into the urethra.
Figure 5:
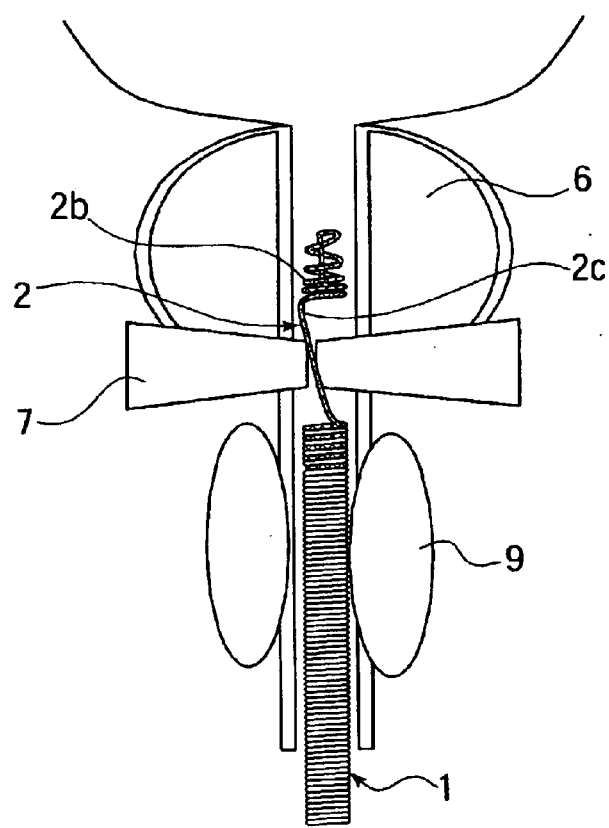

A second embodiment of the implant in accordance with the invention, shown in FIGS. 2–5, is meant to be placed in the area of the male urethra. The implant comprises a helically coiled elongate section 1, which connects to section 2. Section 2 comprises a locking section 2b and a longitudinal rod section 2c having a helically coiled end portion 2a at the first end thereof which can be used to connect section 2 to section 1. The locking section 2b is connected to the second end of the longitudinal rod section 2c and during installation is placed in the area of prostate 6 behind the sphincter muscle of urethra 7 as shown in FIG. 5. The longitudinal rod section 2c traverses the area of the sphincter muscle of urethra 7 as shown in FIG. 5. Due to the compression of the sphincter muscle around section 2c, coupled with the relatively fast expansion of section 2, the placement of the implant is secured and the helically coiled elongate section 1 can function in the desired manner, without risk of migration.

As shown in FIG. 4 the implant is installed by pushing the implant inside the urethra via the external urethral orifice as shown by the arrow 8. It is positioned so that the helically coiled elongate section 1 is placed at the area of an obstruction 9 in the urethra. Section 1, initially held in place by section 2 and later, by its own expansion in vivo, keeps the obstructed portion of the urethra open, until it eventually degrades.

Further aspects of the present invention and its applicability is described in more detail by means of the following nonlimiting examples.

EXAMPLE 1

Figure 2:
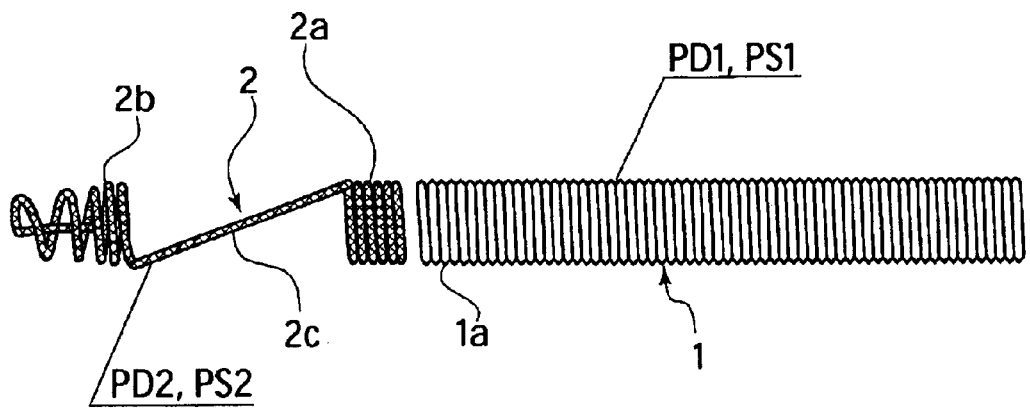
FIG. 2 shows in a side planar view of a second embodiment of an implant according to the invention prior to the connection of the first and second sections.

Polymers chosen from Table 1 were used to prepare helical implants ("stents") in accordance with the present invention, such as those shown in FIGS. 1–3. The stents had the following dimensions: wire thickness, one mm; outer diameter of helix, 8 mm; inner diameter, 6 mm; pitch angle, 15 degrees; and length of implant, 50–100 mm. The stents were made by first subjecting the polymeric melt to extrusion molding to produce filaments having a diameter (Ø) of 1.5–2.0 mm. The filaments were drawn (to induce orientation and self-reinforcement) at a temperature of Tm>T>Tg (wherein Tg is polymer glazing temperature and Tm is polymer melting temperature) to Ø of 1 mm. They were then wound in a hot state around a metal pipe (diameter 5 mm), cooled, and removed from the surface of the metal pipe. The stents were immersed in a $Na_2HPO_4$—$KH_2PO_4$ buffer solution at pH 6.1 and 0.1 M at +37° C. To ensure constant pH, buffer solutions were changed regularly. Three to five stents were removed periodically from the solutions and changes in their mechanical properties were determined. The compression strength of the implants were measured by squeezing an implant between two steel plates with an external force in the direction orthogonal to the implant's longitudinal axis. The implants were compressed until they collapsed or broke down, and the maximum force and the displacement in the direction of compression was measured.

The compression load strengths of implants made of different polymers were compared. The compression load strength (SP) of the implant—a force required to fracture the implant, was determined.

Implants were manufactured from the following biodegradable polymers, copolymers and polymer compositions: polylactide (Mw 120,000), polyglycolide (Mw 60,000), glycolide/lactide copolymer (Mw 40,000), glycolide/trimethylenecarbonate copolymer (Mw 60,000), PLLA (Mw 260,000), PDLLA (Mw 100,000), lactide/δ-valerolactone copolymer (Mw 60,000), lactide/6-caprolactone copolymer (Mw 60,000), PHBA (Mw 700,000), PHPA (Mw 50,000) and PU (Mw 40,000). The initial resulting values for SP ranged between 50N and 430N. The strength retention of SP in the phosphate buffer solution immersion (80% reduction from initial value) ranged from 1 week to 1 year.

EXAMPLE 2

Polymers selected from Table 1 were used to prepare tubular pieces (tube length 10 mm, outer diameter 6 mm and inner diameter 4 mm) by injection molding polymer melt into a cooled tubular mold. The tubes were immersed in $Na_2HPO_4$—$KH_2PO_4$ buffer solution at pH 6.1 and 0.1 M at +37° C. To ensure constant pH, buffer solutions were changed regularly. Three to five tubes were removed periodically from solutions and changes in mechanical properties were determined. The compression strength of the implants was measured by squeezing an implant between two steel plates with an external force in the direction orthogonal to its longitudinal axis. The implant was compressed until it collapsed or broke down and the maximum force and the displacement in the direction of compression was measured.

The compression load strengths of implants made of different polymers were compared. The compression load strength (SP) of the implant—a force required to fracture the implant—was determined. The tubes were manufactured from the following biodegradable polymers, copolymers and polymer compositions: polylactide (Mw 120,000), polyglycolide (Mw 60,000), glycolide/lactide copolymer (Mw 40,000), glycolide/tirimethylenecarbonate copolymer (Mw 60,000), PLLA (Mw 260,000), PDLLA. (Mw 100,000), lactide/ϵ-valerolactone copolymer (Mw 60,000), lactide/ϵ-caprolactone copolymer (Mw 60,000), PHBA (Mw 700,000), PHPA (Mw 50,000) and PDS (Mw 40,000). The initial resulting values for SP ranged between 70 and 410N. The strength retention of SP in the phosphate buffer solution immersion (80% reduction from initial value) ranged from one week to one year.

EXAMPLE 3

Self-reinforced implants as shown in FIG. 1 (herebelow 'stents') were made in a manner similar to that described in example 1. The stents were manufactured from a thick, extruded polymer rod which was drawn to a draw ratio of 4–8 at temperatures between +70–160° C. in order to self-reinforce the material. The self-reinforced rods, having a thickness of 1 mm, were then wound to form "helixes" as described in example 1. The helixes were annealed at temperatures from between +100 to +180° C. for between 1–30 minutes. The stents were then cut into lengths of 50 mm. The stents were immersed in $Na_2HPO_4$, —$KH_2PO_4$, buffer solution at pH 6.1 and 0.1 M at +37° C. To ensure constant pH, buffer solutions were changed regularly. The outside diameters of three stents were measured periodically from three points of the spiral and the changes were determined. The expansion rates of helixes depended on the annealing temperature and annealing time of the stents. The expansion of the self-expanding bioabsorbable stents was greatest during the first few minutes. The fastest expanding stent was made from PLLA. In 30 minutes, the PLLA stent expanded 41%. The initial expansion of the other stents was slower, and ranged from 0% to 66% after 24 hours and from 30% to 150% after 48 hours.

EXAMPLE 4

Self-reinforced implants as shown in FIG. 3 (herebelow 'double stent') were made from polymers selected from Table 1. The double stents were manufactured from thick, extruded polymer rods which were drawn to a draw ratio from 2 to 9 at temperatures from +500° C. to +160° C. in order to self-reinforce the material. The self-reinforced rods, having a thickness of one mm, were then wound to form helixes, as described in example 1. The helixes were annealed as in example 3 to ensure the similar expansion of the two parts of the stents.

The helixes were cut into lengths of 50 mm. The ends of the helixes were screwed together as shown in FIG. 3. The materials were paired following way: helixes that had a faster strength retention loss in the phosphate buffer solution immersion test in example 1 were screwed together with helixes whose strength retention loss was slower. Three to five stents were removed periodically from the solutions and changes in mechanical properties were determined. The compression strength of the implants were measured by squeezing an implant between two steel plates with an external force in the direction orthogonal to its longitudinal axis. The implant was compressed until the construction collapsed or broke down and the maximum force and the displacement in the direction of compression was measured.

Figure 6:
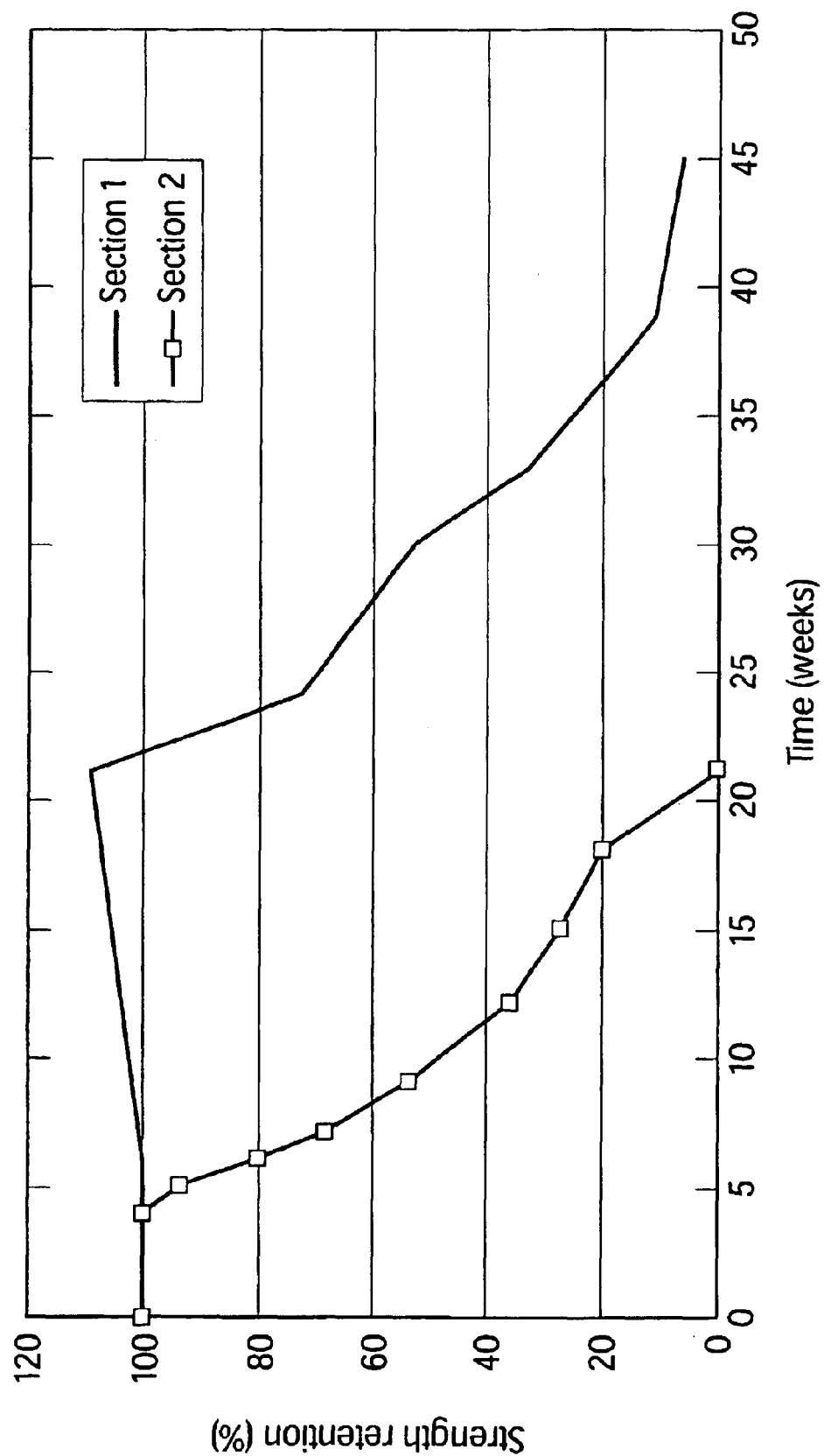
FIG. 6 shows the strength retention curves of the first and second sections of the test implant in accordance with example 4.

The compression load strengths of the two parts of the implant were compared. The compression load strength (SP) of the two parts of the implant—a force required to fracture the implant, was determined. The strength retention curves of sections 1 and 2 are presented in FIG. 6. The initial resulting values for SP ranged between 50 and 430N. The strength retention of SP in the phosphate buffer solution immersion (80% reduction from initial value) ranged from one week to one year. As seen in FIG. 6, the second part of the implant lost strength faster than the first part of the implant.

EXAMPLE 5

A self-reinforced polylactide/glycolide/lactide copolymer implant as shown in FIG. 3 (hereinbelow 'double stent') was prepared using poly-L-lactide (PLLA, Mw 140 000) and glycolide/lactide copolymer (PLGA, lactide/glycolide ratio 80L/20G, Mw=90 000). The double stents were was manufactured from thick, extruded PLLA and PLGA rods which were drawn to a draw ratio of 7 and 4, respectively, at a temperature of 100 and 90 Celcius degrees, respectively, to self-reinforce the material. The self-reinforced PLLA rods having a thickness of 1 mm were then wound to form helixes as described in example 1. The PLGA rods were wound to the form shown in FIG. 1. The helixes were annealed as in example 3 to ensure the similar expansion of the two parts of the stents.

The PLLA helixes were cut into lengths of 50 mm. The ends of the PLGA and PLLA helixes were screwed together. The double stents were immersed in $Na_2HPO_4$, —$KH_2PO_4$ buffer solution at pH 6.1 and 0.1 M at +37° C. To ensure constant pH, buffer solutions were changed regularly. The outside diameters of three stents were measured periodically at four points of the spiral (two points in the PLLA section and two points in the PLGA section) and the changes were determined. The expansion rate of the PLLA section was similar to the PLGA section. The two sections of the double stents stayed together while the expansion occurred.

EXAMPLE 6

Implants of the present invention such as those shown in FIG. 4 (hereinbelow 'double stent') were prepared from a biodegradable polymer matrix containing biodegradable reinforcing fibers. First, a bundle of parallel fibers with fine particulate polymer powder (particle size 1–10 µm) mixed therein was compression molded in a rod-shaped mold (length 8 cm, Ø 1.5 mm) above the melting point (in the case of partially crystalline polymers) or glazing point (in the case of amorphous polymers) of the matrix polymer. The reinforcing fibers were 40–60% by volume. The rods were heated and wound helically around a hot cylindrical mold (outer diameter of helix 8 mm) and the mold was cooled. When using an n-butylcyano acrylate reaction polymer as a matrix, the bundle of reinforcing fibers was rapidly impregnated with cyanoacrylate and the uncured wetted bundle of threads was wound helically around a teflon-coated steel pipe followed by wetting and removing the implant. A corresponding implant was made by using just cyanoacrylate. Impregnation technique was also applied when using a matrix containing segmented polyurethane (S. Gagolewski and A. Perinings, Makromol. Chem. Rapid Coman. 4, 1983, p. 213) which was dissolved in N,N"-dimethylformamide/tetra-hydrofurane solution (weight ratio 3/2). Then, the bundle of fibers helically wound on the surface of a teflon-coated pipe was impregnated at 80 degrees with a polyurethane solution and the pipe was immersed in a mixture of ethanol and distilled water (1:1). This process was repeated several times to prepare the implant. A corresponding implant was made by using just polyurethane. Implants corresponding to such reinforced implants were also manufactured from thermoplastic matrix polymers using known melt working techniques.

Table 2 illustrates the matrix polymers and fibrous reinforcements for the implants prepared.

The expansion rates of the different stents were tested as in example 3. The stents that had similar expansion rates were screwed together as shown in FIG. 3. The double stents were immersed in $Na_2HPO_4$—$KH_2PO_4$, buffer solution at pH 6.1 and 0.1 M at +37° C. To ensure constant pH, buffer solutions were changed regularly. The outside diameters of three stents were measured periodically from four points of the spiral (two points of each part) and the changes were determined. The expansion rates of two parts of the stent were similar and they stayed together when expansion occurred.

EXAMPLE 7

A self-reinforced polylactide/glycolide/lactide copolymer implant as shown in FIG. 3 (herebelow 'double stent') was prepared from poly-L-lactide (PLLA, Mw 140,000) and polyglycolide (PGA, Mw ~90,000). Double stents were manufactured from thick, extruded PLLA and PGA rods which were drawn to a draw ratio of 7 and 4, respectively, at a temperature of 100° and 90° C., respectively, to self-reinforce the material. The self-reinforced PLLA rods, having a thickness of one mm, were then wound to form helixes as described in example 1. The PGA rods were wound to the form of section 2 shown in FIG. 2. The helixes were annealed as in example 3 to ensure the similar expansion of the two sections of the stents. The PLLA helixes were cut into lengths of 50 mm. The PGA and PLLA helixes were screwed together as shown in FIG. 3.

Male dogs were anesthetized with Dormitor® and Ketalar® injections. The dogs' urethra was strictured by suture implantation. After two months the dogs were anesthetized again with Dormitor® and Ketalar® injections. The double stent was inserted in the dogs' urethra in direct vision control using pediatric cystoscope Ch 10. The PLLA section of the double stent was pushed into the strictured area and the PGA section was located partly in the prostate and sphincter area as shown in FIG. 5. The tail part 2c of the double stent was located in the sphincter area and helped to lock the stent in place. After waking up from anesthesia, the dogs were allowed to move freely. The animals were sacrificed after one week, one month, 6 months and one year using Mebunate injection intravenously. The strictured urethra was prepared for investigation. After one week, both sections of the stents were expanded and fixed to the walls of urethra and strictured area was open. After one month, the PGA section had disappeared and the PLLA section was tightly affixed to the strictured area. At six months, the PLLA section had incorporated into the urethral tissue and the urethra was open and normal in volume. After one year, the PLLA section had nearly disappeared and the urethra had a normal extent and volume and the stricture was no longer macroscopically observable.

EXAMPLE 8

The polymers set forth in table 1 can be used to prepare tubular pieces (e.g., tube length 10 mm, outer diameter 6 mm and inner diameter 4 mm), e.g., by injection molding polymer melt into a cooled tubular mold. The tubes can also be connected to the helixes described in example 1, to form an implant.

The materials can be paired in the following way: the material (tube or helix) that has faster strength retention loss in phosphate buffer solution is connected together with material (tubes or helix) whose strength retention loss is slower. Three to five of these samples were removed periodically from phosphate buffer solutions and any changes in mechanical properties were determined.

The compression strength of the implants was measured by squeezing an implant between two steel plates with an external force in the direction orthogonal to its longitudinal axis. The implant is compressed until it collapses or breaks down and the maximum force and the displacement in the direction of compression were measured.

The compression load strengths of the two sections of the implant are determined and compared to each other. The compression load strength (SP) is the force required to fracture the implant. The strength retention curves of sections 1 and 2 are presented in FIG. 7. The initial resulting values for SP typically range between 60 and 360N. The strength retention of SP in phosphate buffer solution immersion (80% reduction from initial value) ranges typically from one week to one year. Section 1 lasted longer than section 2.

The geometries of the sections of the implants of the present invention are not limited to those shown in the figures and examples. Other geometries would suggest themselves to those of skill in the art. For instance, the references cited at the beginning of the specification, namely U.S. Pat. No. 5,792,400 to Talja et al. and WO 97/11724 to Törmälä et al. present various useful modifications, which can also be applied in connection with the present invention. Thus, conical shapes of the implant can be used instead of or together with the cylindrical ones shown in the Figs of the present invention. Additionally various cross sectional shapes as shown in FIGS. 11a–11f of U.S. Pat. No. 5,792,400 can be used. Also, more than two sections can be used to form implants of the present invention, depending upon the particular application.

TABLE 1

Biodegradable polymers

| | |
|---|---|
| 1. | Polyglycolide (PGA) |
| | Copolymers of glycolide |
| 2. | Glycolide/lactide copolymers (PGA/PLA) |
| 3 | Glycolide/trimethylene carbonate copolymers (PGA/TMC) |
| | Polylactides (FLA) |
| | Stereoisomers and copolymers of PLA |
| 4. | Poly-L-lactide (PLLA) |
| 5. | Poly-D-lactide (PDLA) |
| 6. | Poly-DL-lactide (PDLLA) |
| 7. | L-lactide/DL-lactide copolymers |
| | L-lactide/D-lactide copolymers |
| | Copolymers of PLA |
| 8. | Lactide/tetramethylene glycolide copolymers |
| 9. | Lactide/trimethylene carbonate copolymers |
| 10. | Lactide/δ-valerolactone copolymers |
| 11. | Lactide/∈-caprolactone copolymers |
| 12. | Polydepsipeptides (glycine-DL-lactide copolymer) |
| 13. | PLA/ethylene oxide copolymers |
| 14. | Asymmetrically 3,6-substituted poly-1,4-dioxane-2,5-diones |
| 15. | Poly-β-hydroxybutyrate (PHBA) |
| 16. | PHBA/β-hydroxyvalerate copolymers (PHBA/PHVA) |
| 17. | Poly-β-hydroxypropionate (PHPA) |
| 18. | Poly-β-dioxanone (PDS) |
| 19. | Poly-δ-valerolactone |
| 20. | Poly-∈-caprolactone |
| 21. | Methylmethacrylate-N-vinylpyrrolidone copolymers |
| 22. | Polyesteramides |
| 23. | Polyesters of oxalic acid |
| 24. | Polydihydropyranes |
| 25. | Polyalkyl-2-cyanoacrylates |
| 26. | Polyuretanes (PU) |
| 27. | Polyvinyl alcohol (PVA) |
| 28. | Polypeptides |
| 29. | Poly-β-maleic acid (PMLA) |
| 30. | Poly-(β-alkanoic acids |
| 31. | Polyethylene oxide (PEO) |
| 32. | Chitin polymers |

TABLE 2

Structural components for fibre-reinforced biodegradable implants.

| Matrix polymer | Fibre reinforcement |
|---|---|
| PDS | PGA |
| " | PGA/TMC |
| " | PGA/PLLA |
| " | PLLA |
| " | PHBA |
| " | PHBA/HVA |
| " | Chitin fibre |
| " | PDS |
| PDLLA | PGA |
| " | PGA/TMC |
| " | PGA/PLLA |
| " | PLLA |
| " | PHBA |
| " | PHBA/KVA |
| " | PDS |
| " | PDLLA |

TABLE 2-continued

Structural components for fibre-reinforced
biodegradable implants.

| Matrix polymer | Fibre reinforcement |
| --- | --- |
| PLLA | PGA |
| " | PGA/TMC |
| " | PLLA |
| PVA | PGA |
| " | PGA/TMC |
| " | PGA/PLLA |
| " | PLLA |
| " | PHBA |
| " | PHBA/HVA |
| " | PDS |
| " | Chitin fibres |
| PGA/TMC | PGA |
| " | PGA/TMC |
| PHBA | PGA |
| " | PGA/TMC |
| " | PHBA |
| Poly-∈-caprlactone | PGA |
| " | PGA/TMC |
| " | PHBA |
| Methymetacrylate-N-vinylpyrrolidone | PGA |
| Polyurethane | PGA |
|  | Collagen (catgut) |
| PEO | PGA |
| " | PGA/TMC |
| " | PGA/PLA |
| " | PLLA |
| n-Butylcyano-acrytate | Collagen (catgut) |
|  | PGA |

We claim:

1. A biodegradable implant for installation in living tissue comprising a first proximal section made from a first bioabsorbable material and a second distal section made from a second bioabsorbable material different from said first bioabsorbable material, said second distal section having at least a longitudinal portion disposed separately from said first proximal section, wherein said first proximal section and said second distal section are connected, said first proximal section having a first rate of degradation in living tissue and a first rate of self expansion in living tissue and said second distal section having a second rate of degradation in living tissue and a second rate of self expansion in living, wherein said second rate of self expansion is different and independant from said first rate of self expansion tissue.

2. The biodegradable implant of claim 1, wherein said first rate of degradation is slower than said second rate of degradation.

3. The biodegradable implant of claim 1, wherein said first rate of self expansion is slower than said second rate of self expansion.

4. The biodegradable implant of claim 2, wherein said first rate of self expansion is slower than said second rate of self expansion.

5. The biodegradable implant of claim 1, wherein at least one of said sections comprises a helical structure.

6. The biodegradable implant of claim 1, wherein at least one of said sections comprises a tubular structure.

7. The biodegradable implant of claim 1, wherein one of said sections comprises a helical structure and one of said sections comprises a tubular structure.

8. The biodegradable implant of claim 5, wherein said sections are connected by intertwined helical structures.

9. The biodegradable implant of claim 1, wherein said second distal section comprises: a connecting section for connecting said second distal section to said first proximal section, an locking section having a cross section that is wide enough to lock said second distal section in place in vivo, and a intermediate section that connects said locking section to said connecting section.

10. The biodegradable implant of claim 9 wherein said connecting section comprises a helical structure.

11. The biodegradable implant of claim 10 wherein said locking section comprises a helical structure.

12. The biodegradable implant of claim 11 wherein said intermediate section has a narrower cross section than said connecting section and said locking section.

13. The biodegradable implant of claim 1, wherein said implant is a stent.

14. The biodegradable implant of claim 1, wherein said rate of self expansion of at least one of said sections is caused by swelling of said material.

15. The biodegradable implant of claim 1, wherein said first section comprises polyglycolic acid and said second section comprises poly-L-lactic acid.

16. A biodegradable implant comprising a first proximal section comprising a first material, said first proximal section being connected to a second distal section comprising a second material different from said first material, said second distal section having at least a longitudinal portion disposed separately from said first proximal section, said first proximal section and said second distal section being capable of expanding self, in vivo, at different and independant rates, such that said first proximal section expands quicker than said second distal section when placed in vivo and then degrades after said second distal section expands.

17. The biodegradable implant of claim 16 wherein at least one of said sections comprises a helical structure.

18. The biodegradable implant of claim 16 wherein at least one of said sections comprises a tubular structure.

19. The biodegradable implant of claim 17 wherein said sections are connected by intertwined helical structures.

20. The biodegradable implant of claim 16, wherein said self expansion of at least one of said sections is caused by swelling of said material.

21. The biodegradable implant of claim 16 wherein said self expansion helps prevent said implant from migrating in vivo.

22. The biodegradable implant of claim 21 wherein said implant is a urethral stent.

23. The biodegradable implant of claim 22 wherein said implant can withstand compression forces of at least 50N.

* * * * *